(12) United States Patent
Taguchi et al.

(10) Patent No.: US 9,456,790 B2
(45) Date of Patent: Oct. 4, 2016

(54) X-RAY COMPUTED TOMOGRAPHY IMAGING APPARATUS AND PHOTON COUNTING CT APPARATUS

(71) Applicant: Toshiba Medical Systems Corporation, Otawara-shi (JP)

(72) Inventors: Hiroki Taguchi, Otawara (JP); Satoru Nakanishi, Arlington Heights, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 201 days.

(21) Appl. No.: 14/454,085

(22) Filed: Aug. 7, 2014

(65) Prior Publication Data
US 2015/0063529 A1 Mar. 5, 2015

(30) Foreign Application Priority Data
Aug. 30, 2013 (JP) .................................. 2013-180725

(51) Int. Cl.
*A61B 6/00* (2006.01)
*A61B 6/03* (2006.01)
*G06T 11/00* (2006.01)

(52) U.S. Cl.
CPC .............. *A61B 6/032* (2013.01); *A61B 6/4241* (2013.01); *A61B 6/482* (2013.01); *A61B 6/52* (2013.01); *A61B 6/5205* (2013.01); *G06T 11/005* (2013.01); *G06T 2211/408* (2013.01)

(58) Field of Classification Search
CPC ........ A61B 6/032; A61B 6/482; A61B 6/52; A61B 6/4241; A61B 6/5205; G06T 11/005; G06T 2211/408
USPC ....................................................... 378/4–20
See application file for complete search history.

(56) References Cited

FOREIGN PATENT DOCUMENTS

| JP | 2009-95405 | 5/2009 |
|----|------------|--------|
| JP | 2009-112627 | 5/2009 |
| JP | 2009-261942 | 11/2009 |
| JP | 2013-56149 | 3/2013 |

*Primary Examiner* — Courtney Thomas
(74) *Attorney, Agent, or Firm* — Oblon, McClelland, Maier & Neustadt, L.L.P.

(57) ABSTRACT

Based on a plurality of detection data sets acquired by a data acquisition unit and correspond to respective tube voltages, an image generator generates a plurality of reference substance image data sets targeting respective reference substances contained in a subject. The image generator generates a correction data set for each of the plurality of tube voltages by applying, to a detection data set corresponding to each of the tube voltages, a correction coefficient for suppressing a discrepancy of an actual energy spectrum of the X-rays detected by an X-ray detector from a predetermined X-ray energy spectrum, and generates the plurality of reference substance image data sets based on a plurality of correction data sets corresponding to the respective tube voltages.

12 Claims, 3 Drawing Sheets

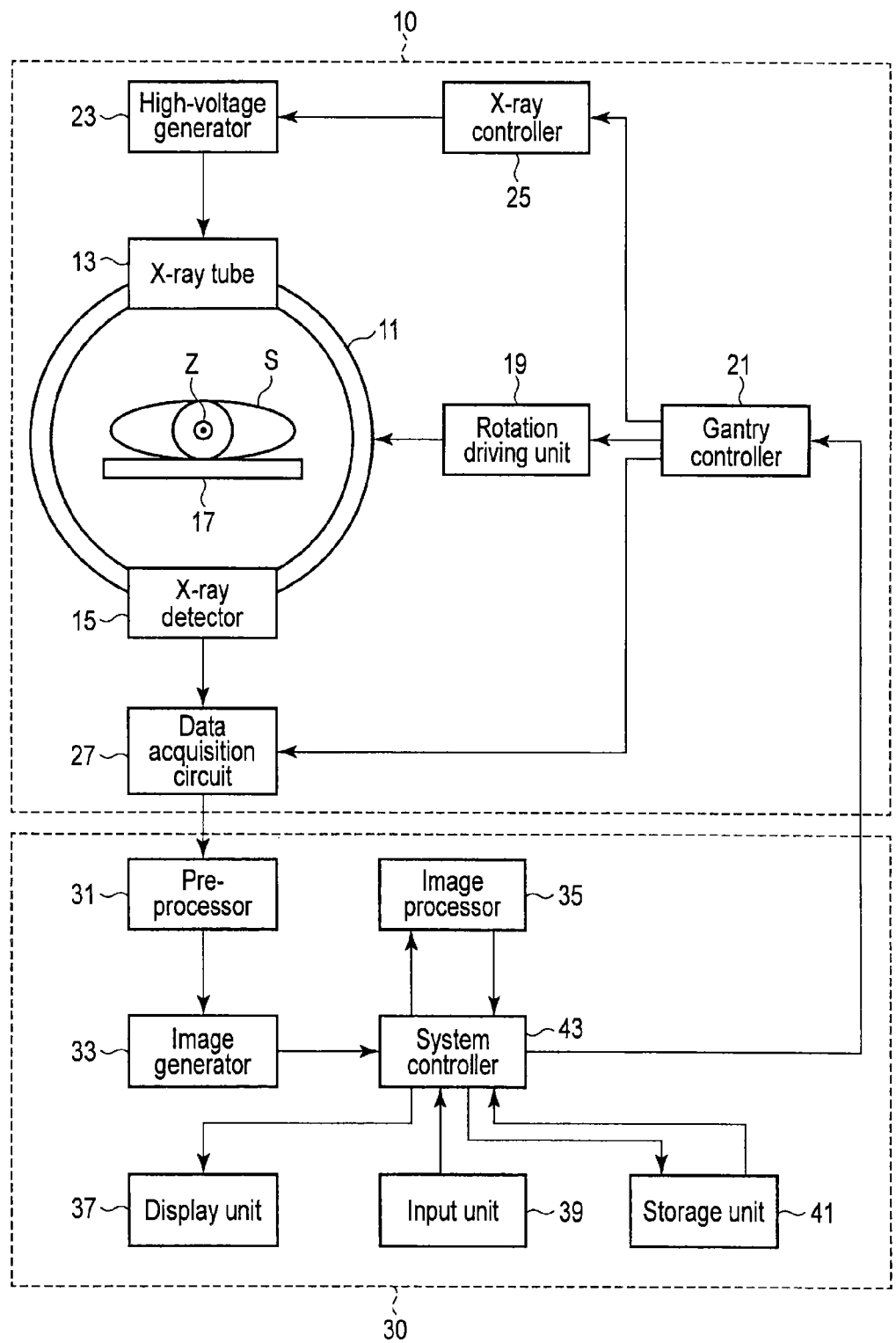
F I G. 1

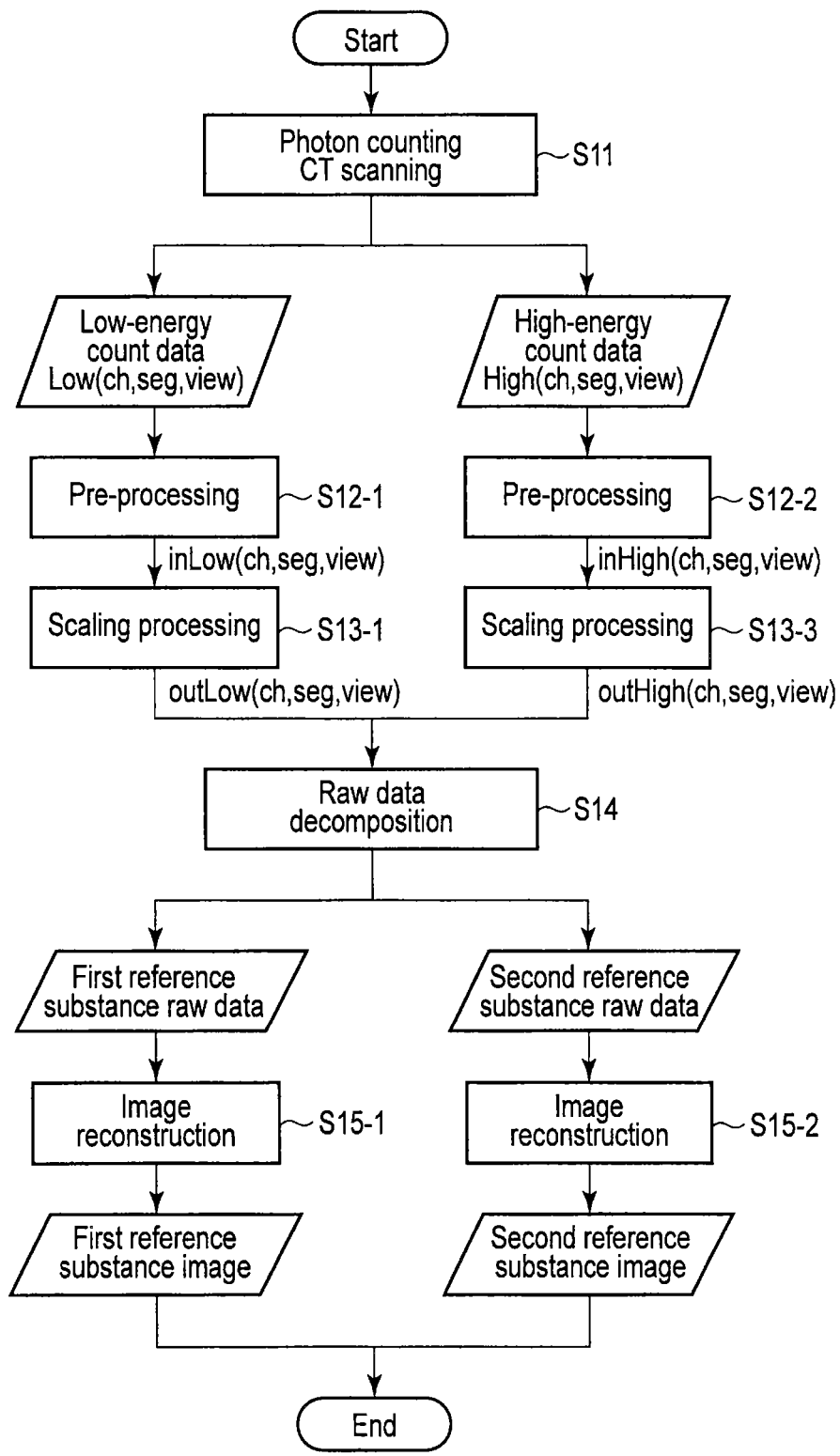
F I G. 3

X-RAY COMPUTED TOMOGRAPHY IMAGING APPARATUS AND PHOTON COUNTING CT APPARATUS

CROSS-REFERENCE TO RELATED APPLICATIONS

This application is based upon and claims the benefit of priority from the prior Japanese Patent Application No. 2013-180725, filed Aug. 30, 2013 the entire contents of which are incorporated herein by reference.

FIELD

Embodiments described herein relate generally to an X-ray computed tomography imaging apparatus and photon counting CT apparatus.

BACKGROUND

A scanning method using a plurality of types of different tube voltages, that is, multi-energy CT scanning has been developed for X-ray computed tomography imaging apparatuses. Multi-energy CT scanning includes a scanning method using two tube voltages, that is, dual-energy CT scanning. An application of dual-energy CT scanning is raw data decomposition of generating two types of raw data (to be referred to as reference substance data hereinafter) about two reference substances set in advance by using raw data derived from X-rays generated at a low tube voltage, and raw data derived from X-rays generated at a high tube voltage. Data of an image (to be referred to as a reference substance image hereinafter) targeting the first reference substance is generated based on the first reference substance data, and the second reference substance image data is generated based on the second reference substance data.

In raw data decomposition, a known X-ray spectrum is used. Ideally, the energy spectrum of X-rays generated from an X-ray tube should be constant. In practice, however, the X-ray spectrum sometimes shifts by about several kV. Owing to the discrepancy of an actual X-ray energy spectrum from an ideal X-ray energy spectrum, the accuracy of raw data decomposition degrades. As a result, the qualities of a reference substance image, a monochromatic X-ray image and density image based on the reference substance, and an effective atomic number image degrade.

In image reconstruction in a normal scanning method using a single tube voltage (to be referred to as single-energy CT scanning hereinafter), scaling processing is performed to suppress the discrepancy of an actual X-ray energy spectrum from an ideal X-ray energy spectrum. When scaling processing in single-energy CT scanning is applied to dual-energy CT scanning, the scaling processing is performed at the time of image reconstruction after raw data decomposition. However, raw data after raw data decomposition does not have CT value information, so the scaling processing in single-energy CT scanning cannot be applied to dual-energy CT scanning.

An object of an embodiment is to provide an X-ray computed tomography imaging apparatus and photon counting CT apparatus capable of suppressing deterioration of the image quality arising from the discrepancy of an actual X-ray energy spectrum from an ideal X-ray energy spectrum.

BRIEF DESCRIPTION OF THE DRAWINGS

FIG. 1 is a view showing the arrangement of an X-ray computed tomography imaging apparatus according to an embodiment;

FIG. 3 is a flowchart showing an example of the typical operation of photon counting CT scanning to be performed under the control of the system controller according to the second modification of the embodiment.

DETAILED DESCRIPTION

Figure 2:
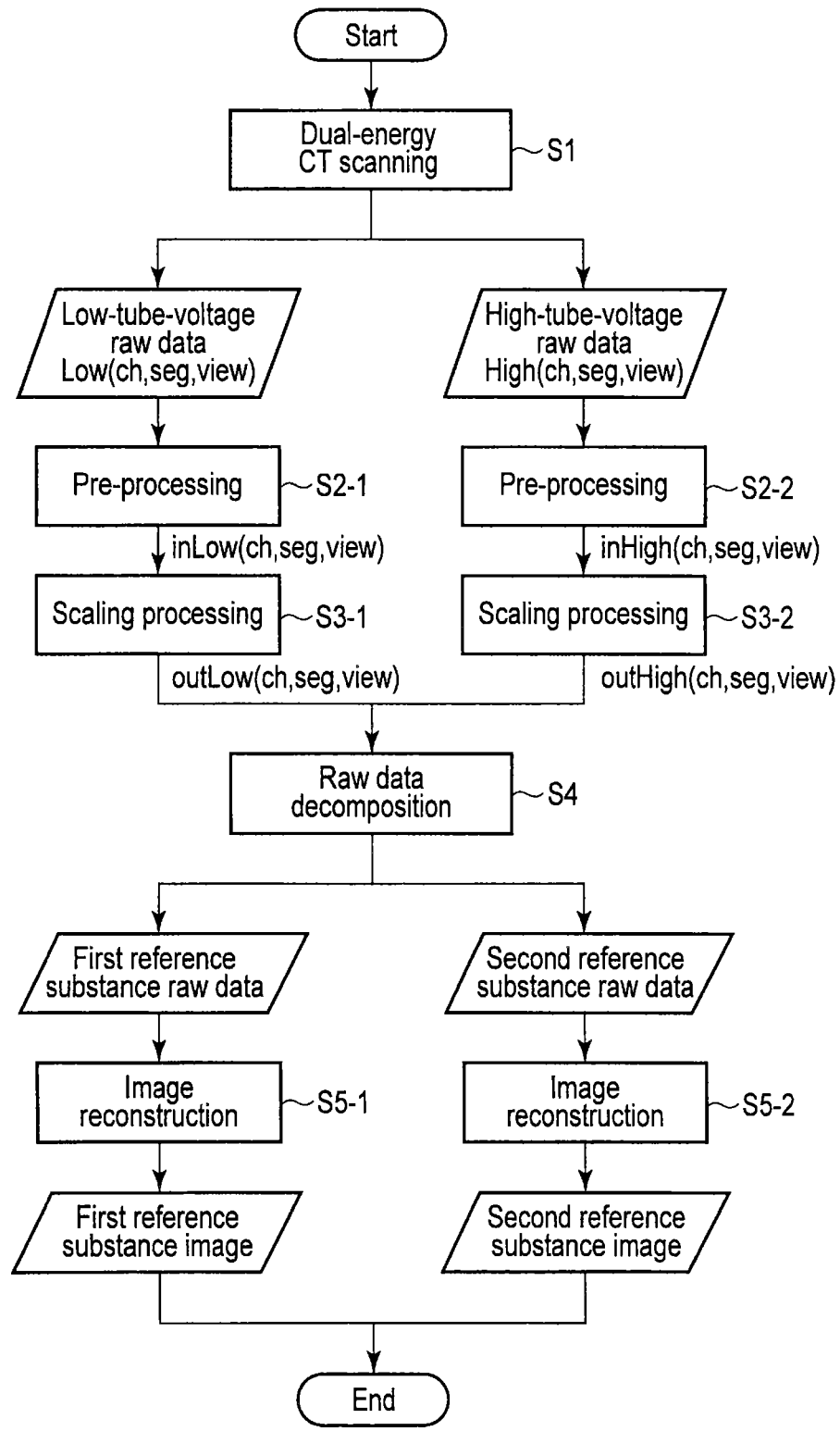
FIG. 2 is a flowchart showing an example of the typical operation of dual-energy CT scanning to be performed under the control of a system controller in FIG. 1.

An X-ray computed tomography imaging apparatus according to an embodiment comprises an X-ray tube, high-voltage generator, X-ray detector, support mechanism, data acquisition unit, and image generator. The X-ray tube generates X-rays. The high-voltage generator generates a tube voltage to be applied to the X-ray tube. The X-ray detector detects X-rays which have been generated from the X-ray tube and have passed through a subject. The support mechanism rotatably supports the X-ray tube. The data acquisition unit acquires detection data corresponding to an intensity of the detected X-rays via the X-ray detector. Based on a plurality of detection data sets which have been acquired by the data acquisition unit and correspond to respective tube voltages, the image generator generates a plurality of reference substance image data sets targeting respective reference substances contained in the subject. The image generator generates a correction data set for each of the plurality of tube voltages by applying, to a detection data set corresponding to each of the tube voltages, a correction coefficient for suppressing a discrepancy of an actual energy spectrum of the X-rays detected by the X-ray detector from a predetermined X-ray energy spectrum, and generates the plurality of reference substance image data sets based on a plurality of correction data sets corresponding to the respective tube voltages.

An X-ray computed tomography imaging apparatus and photon counting CT apparatus according to the embodiment will now be described with reference to the accompanying drawings.

FIG. 1 is a view showing the arrangement of an X-ray computed tomography imaging apparatus 1 according to the embodiment. As shown in FIG. 1, the X-ray computed tomography imaging apparatus 1 includes a gantry 10 and console 30. The gantry 10 supports a rotating frame 11 having a cylindrical shape so that the rotating frame 11 can rotate about a rotation axis Z. An X-ray tube 13 and X-ray detector 15 are attached to the rotating frame 11 so that they face each other via the rotation axis Z. The opening of the rotating frame 11 is set to an FOV (Field Of View). A top 17 is inserted in the opening of the rotating frame 11. A Subject S is placed on the top 17. The top 17 is positioned so that the imaging portion of the subject S on the top 17 falls in the FOV. The rotating frame 11 rotates at a predetermined angular velocity about the rotation axis Z upon receiving power from a rotation driving unit 19. The rotation driving unit 19 generates power for rotating the rotating frame 11 in accordance with a drive signal from a gantry controller 21.

The X-ray tube 13 is connected to a high-voltage generator 23. The X-ray tube 13 generates X-rays upon receiving the application of a tube voltage from the high-voltage generator 23, and the supply of a filament current. The high-voltage generator 23 applies, to the X-ray tube 13, a tube voltage having a voltage value corresponding to control by an X-ray controller 25, and adjusts a tube current in the X-ray tube 13 to a current value corresponding to control by the X-ray controller 25. The X-ray controller 25 controls the high-voltage generator 23 under the control of the gantry controller 21.

The X-ray detector 15 detects X-rays which have been generated from the X-ray tube 13 and have passed through the subject S. The X-ray detector 15 includes a plurality of X-ray detection elements arrayed two-dimensionally. Each X-ray detection element detects X-rays from the X-ray tube 13, and generates an electrical signal corresponding to the energy of the detected X-rays.

Under the control of the gantry controller 21, a data acquisition circuit 27 acquires, via the X-ray detector 15, digital data corresponding to the energy of X-rays detected by the X-ray detector 15. More specifically, under the control of the gantry controller 21, the data acquisition circuit 27 acquires electrical signals from the respective X-ray detection elements for each view, and converts the acquired electrical signals into digital data. The converted digital data is called raw data. The raw data is supplied to the console 30.

The gantry controller 21 supervises the control of various devices mounted in the gantry 10 in accordance with an instruction from a system controller 43 in the console 30. For example, the gantry controller 21 performs centralized control of the rotation driving unit 19, X-ray controller 25, and data acquisition circuit 27 to execute multi-energy CT scanning. The rotation driving unit 19 rotates at a predetermined angular velocity under the control of the gantry controller 21. Under the control of the gantry controller 21, the X-ray controller 25 controls the high-voltage generator 23 to sequentially apply, to the X-ray tube 13, tube voltages having a plurality of tube voltage values set in advance. Under the control of the gantry controller 21, the data acquisition circuit 27 acquires raw data for each view in synchronism with the X-ray exposure timing.

The console 30 includes a pre-processor 31, an image generator 33, an image processor 35, a display unit 37, an input unit 39, a storage unit 41, and the system controller 43.

The pre-processor 31 performs pre-processing such as logarithmic transformation on raw data from the gantry 10. Raw data after pre-processing is also called projection data. The pre-processing includes various correction processes such as logarithmic transformation, X-ray intensity correction, and offset correction.

Based on a plurality of raw data sets corresponding to respective tube voltages, the image generator 33 generates a plurality of reference substance image data sets targeting respective reference substances contained in the subject S. The raw data set is assumed to represent raw data sets by the number of views necessary for reconstruction. The reference substance is assumed to be set in advance via the input unit 39 or the like. More specifically, the image generator 33 generates a correction data set for each of a plurality of tube voltages by applying, to a raw data set corresponding to each tube voltage, a correction coefficient for suppressing the discrepancy of the actual energy spectrum of X-rays detected by the X-ray detector 15 from a predetermined X-ray energy spectrum. Then, the image generator 33 generates a plurality of reference substance image data sets based on a plurality of correction data sets corresponding to the respective tube voltages. The predetermined X-ray energy spectrum is, e.g., an ideal energy spectrum acquired in advance. The predetermined X-ray energy spectrum may be an actually measured energy spectrum acquired in advance by scanning, or an energy spectrum calculated by simulation.

To acquire an ideal energy spectrum, calibration scanning targeting an arbitrary phantom may be performed. The phantom in this case is, e.g., a water-containing phantom, an air-containing phantom, or a calibration phantom for adjusting a CT value. The pre-processor 31, system controller 43, or the like calculates an energy spectrum based on raw data acquired by the data acquisition circuit 27 under calibration scanning. The storage unit 41 stores data of the energy spectrum as an ideal energy spectrum.

Based on a plurality of reference substance image data sets, the image processor 35 generates a monochromatic X-ray image data set, density image data set, and effective atomic number image data set. The monochromatic X-ray image is an image which is considered to be acquired by exposure to monochromatic X-rays, and expresses the spatial distribution of the CT value. The density image is an image expressing the spatial distribution of the electron density of a substance. The effective atomic number image is an image expressing the spatial distribution of the effective atomic number of a substance.

The display unit 37 displays, on a display device, medical images such as a reference substance image, monochromatic X-ray image, density image, and effective atomic number image. As the display device, for example, a CRT display, liquid crystal display, organic EL display, or plasma display is appropriately available.

The input unit 39 accepts various instructions and information inputs from the user via an input device. As the input device, for example, a keyboard, mouse, or various switches are available.

The storage unit 41 is a main memory which stores various kinds of information. For example, the storage unit 41 stores a raw data set, reference substance image data set, monochromatic X-ray image data set, density image data set, effective atomic number image data set, and the like. Also, the storage unit 41 stores a multi-energy CT scan program according to the embodiment.

The system controller 43 functions as the center of the X-ray computed tomography imaging apparatus 1. The system controller 43 reads out the multi-energy CT scan program according to the embodiment from the storage unit 41, and controls various building components in accordance with the readout program. As a result, multi-energy CT scanning according to the embodiment is executed.

Next, an example of the operation of multi-energy CT scanning according to the embodiment will be explained. As multi-energy CT scanning according to the embodiment, any scanning method is applicable as long as X-rays are generated from the X-ray tube 13 upon applying two or more types of tube voltages. However, to concretely explain the embodiment, multi-energy CT scanning according to the embodiment is assumed to be dual-energy CT scanning. The dual-energy CT scanning is a scanning method of generating X-rays from the X-ray tube 13 upon applying two types of tube voltages, and acquiring, by the data acquisition circuit 27, raw data (to be referred to as low-tube-voltage raw data hereinafter) upon applying a low tube voltage, and raw data (to be referred to as high-tube-voltage raw data hereinafter) upon applying a high tube voltage.

FIG. 2 is a flowchart showing an example of the typical operation of dual-energy CT scanning to be performed under the control of the system controller 43. As shown in FIG. 2, the system controller 43 controls the gantry controller 21 to execute dual-energy CT scanning (step S1). In step S1, the gantry controller 21 starts dual-energy CT scanning in response to a start instruction from the user via the input unit 39 or the like. In dual-energy CT scanning, the gantry controller 21 controls the rotation driving unit 19 to rotate the rotating frame 11 at a predetermined angular velocity. Also, the gantry controller 21 controls the X-ray controller 25 to control the high-voltage generator 23 so as to alternately apply a preset low tube voltage and high tube voltage to the X-ray tube 13. Note that the low tube voltage and high tube voltage may be alternately applied to the X-ray tube 13 for each view, or alternately applied to the X-ray tube 13 for each cycle. The gantry controller 21 controls the data acquisition circuit 27 to acquire a low-tube-voltage raw data set Low(ch,seg,view) in a view in which a low tube voltage was applied, and acquire a high-tube-voltage raw data set High(ch,seg,view) in a view in which a high tube voltage was applied. The low-tube-voltage raw data set Low(ch,seg,view) and high-tube-voltage raw data set High(ch,seg,view) are represented as functions each of a channel (readout channel of the X-ray detector 15) "ch", a segment (X-ray detection element array of the X-ray detector 15) "seg", and a view "view".

Note that the method of alternately acquiring low-tube-voltage raw data and high-tube-voltage raw data for each cycle is called a double-rotation method (Slow-kV switching method). The method of alternately acquiring low-tube-voltage raw data and high-tube-voltage raw data for each view is called a high-speed switching method (Fast-kV switching method). As described above, the embodiment is applicable to both the double-rotation method (Slow-kV switching method) and high-speed switching method (Fast-kV switching method).

After performing step S1, the system controller 43 controls the pre-processor 31 to perform pre-processing (step S2). In step S2-1, the pre-processor 31 performs pre-processing on the low-tube-voltage raw data set from the data acquisition circuit 27, and outputs a low-tube-voltage raw data set inLow(ch,seg,view) after pre-processing. Similarly, in step S2-2, the pre-processor 31 performs pre-processing on the high-tube-voltage raw data set from the data acquisition circuit 27, and outputs a high-tube-voltage raw data set inHigh(ch,seg,view) after pre-processing.

After performing step S2, the system controller 43 controls the image generator 33 to perform scaling processing (step S3). In step S3-1, the image generator 33 multiplies, by a correction coefficient, the low-tube-voltage raw data set inLow(ch,seg,view) after pre-processing, and outputs a low-tube-voltage raw data set outLow(ch,seg,view) after scaling processing. Similarly, in step S3-2, the image generator 33 multiplies, by a correction coefficient, the high-tube-voltage raw data set inHigh(ch,seg,view) after pre-processing, and outputs a high-tube-voltage raw data set outHigh(ch,seg,view) after scaling processing.

The image generator 33 determines the correction coefficient for each voltage value of the tube voltage to be applied to the pre-processor 31. The correction coefficient is a coefficient for suppressing a noise component arising from the energy difference of the actual energy spectrum of X-rays from an ideal energy spectrum for each tube voltage. The correction coefficient is defined by the ratio of a scaling coefficient targeting the ideal energy spectrum of X-rays at each tube voltage to a scaling coefficient targeting the energy spectrum of X-rays actually detected by the X-ray detector 15. The scaling coefficient may be a coefficient at any one of stages from the data acquisition stage by the data acquisition circuit 27 to the reconstruction stage by the image generator 33. For example, at the data acquisition stage, the scaling coefficient is defined to be a magnification for making the data value of raw data in an actual energy spectrum coincide with the data value of raw data in an ideal energy spectrum. For example, at the reconstruction stage, the scaling coefficient is defined to be a magnification for making the CT value of raw data in an actual energy spectrum coincide with the CT value of raw data in an ideal energy spectrum. This magnification is also called a back projection magnification.

A correction coefficient RawScaleLow for a low tube voltage is defined by the following equation (1), and a correction coefficient RawScaleHigh for a high tube voltage is defined by the following equation (2):

$$RawScaleLow = \frac{IdealBpScaleLow}{MeasuredBpScaleLow} \quad (1)$$

$$RawScaleHigh = \frac{IdealBpScaleHigh}{MeasuredBpScaleHigh} \quad (2)$$

As represented by equation (1), the correction coefficient RawScaleLow for a low tube voltage is defined by the ratio of an ideal scaling coefficient IdealBpScaleLow regarding a low tube voltage to an actual scaling coefficient MeasuredBpScaleLow regarding a low tube voltage. As represented by equation (2), the correction coefficient RawScaleHigh is defined by the ratio of an ideal scaling coefficient IdealBpScaleHigh regarding a high tube voltage to an actual scaling coefficient MeasuredBpScaleHigh regarding a high tube voltage.

The ideal scaling coefficient IdealBpScaleLow regarding a low tube voltage is a scaling coefficient targeting the ideal energy spectrum of X-rays generated by applying a low tube voltage to the X-ray tube 13. Similarly, the ideal scaling coefficient IdealBpScaleHigh regarding a high voltage is a scaling coefficient targeting the ideal energy spectrum of X-rays generated by applying a high tube voltage to the X-ray tube 13. The ideal energy spectrum means, e.g., the energy spectrum of direct X-rays generated from the X-ray tube 13. The ideal scaling coefficient IdealBpScaleLow regarding a low tube voltage, and the ideal scaling coefficient IdealBpScaleHigh regarding a high tube voltage are preferably determined in advance by simulation by the image generator 33.

The actual scaling coefficient MeasuredBpScaleLow regarding a low tube voltage is a scaling coefficient targeting low-tube-voltage raw data derived from X-rays which have been generated from the X-ray tube 13 upon applying a low tube voltage to the X-ray tube 13, and have been detected by the X-ray detector 15. An energy spectrum expressed by low-tube-voltage raw data derived from actually detected X-rays exhibits an energy shift of about several kV from an ideal low-tube-voltage energy spectrum. The scaling coefficient MeasuredBpScaleLow is calculated by a known calculation method based on an original low-tube-voltage raw data set acquired by the data acquisition circuit 27, and low-tube-voltage raw data sets before and after pre-processing by the pre-processor 31. The scaling coefficient MeasuredBpScaleLow may be determined in consideration of the tube voltage value, reconstruction function, and the like in addition to these low-tube-voltage raw data sets.

Similarly, the actual scaling coefficient MeasuredBpScaleHigh regarding a high tube voltage is a scaling coefficient targeting high-tube-voltage raw data derived from X-rays of an actual energy spectrum obtained by applying a high tube voltage to the X-ray tube 13. An energy spectrum expressed by high-tube-voltage raw data derived from actually detected X-rays exhibits an energy shift from an ideal high-tube-voltage energy spectrum. The scaling coefficient MeasuredBpScaleHigh is calculated by a known calculation method based on original high-tube-voltage raw data acquired by the data acquisition circuit 27, and high-tube-voltage raw data after pre-processing by the pre-processor 31. The scaling coefficient MeasuredBpScaleHigh may be determined in consideration of the tube voltage value, reconstruction function, and the like in addition to these high-tube-voltage raw data sets.

After the correction coefficient RawScaleLow is determined in this manner, the image generator 33 applies the correction coefficient RawScaleLow to the low-tube-voltage raw data inLow(ch,seg,view) after pre-processing, and outputs low-tube-voltage raw data outLow(ch,seg,view) after scaling processing, as represented by the following equation (3). In the low-tube-voltage raw data outLow(ch,seg,view) after scaling processing, a noise component is suppressed, which is contained in the low-tube-voltage raw data inLow (ch,seg,view) after pre-processing and arises from the energy difference between an ideal energy spectrum and an actual energy spectrum. Similarly, the image generator 33 applies the correction coefficient RawScaleHigh to the high-tube-voltage raw data inHigh(ch,seg,view) after pre-processing, and outputs high-tube-voltage raw data outHigh(ch, seg,view) after scaling processing, as represented by the following equation (4). In the high-tube-voltage raw data outHigh(ch,seg,view) after scaling processing, a noise component is suppressed, which is contained in the high-tube-voltage raw data inHigh(ch,seg,view) after pre-processing and arises from the energy difference between an ideal energy spectrum and an actual energy spectrum.

$$\text{OutLaw(ch,seg,view)}=\text{inLow(ch,seg,view)}\cdot\text{RawScaleLow} \quad (3)$$

$$\text{OutHigh(ch,seg,view)}=\text{inHigh(ch,seg,view)}\cdot\text{RawScaleHigh} \quad (4)$$

In equations (1) and (2) described above, the correction coefficient RawScaleLow for a low tube voltage, and the correction coefficient RawScaleHigh for a high tube voltage are constants. However, the embodiment is not limited to this. For example, the correction coefficients RawScaleLow and RawScaleHigh may be determined for each channel, each X-ray detection element array, and each view. This further improves the correction accuracy of the correction coefficients RawScaleLow and RawScaleHigh.

After performing step S3, the system controller 43 controls the image generator 33 to perform raw data decomposition (step S4). In step S4, the image generator 33 performs raw data decomposition on the low-tube-voltage raw data outLow(ch,seg,view) after scaling processing and the high-tube-voltage raw data outHigh(ch,seg,view) after scaling processing, thereby generating a first data set (to be referred to as a first reference substance raw data set hereinafter) corresponding to the first reference substance, and a second data set (to be referred to as a second reference substance raw data set hereinafter) corresponding to the second reference substance. As the reference substance, any substance present in the subject S is applicable via the input unit 39 by the user. For example, the first reference substance and second reference substance are properly selectable from water, fat, bone (calcium), iodine, and the like. Raw data decomposition suffices to use a known method. Hence, a detailed description of raw data decomposition will be omitted.

As described above, raw data decomposition targets the low-tube-voltage raw data set and high-tube-voltage raw data set multiplied by the correction coefficients for suppressing a noise component arising from the energy difference of the actual energy spectrum of X-rays from an ideal energy spectrum. That is, a raw data set in which the discrepancy of the actual energy spectrum of X-rays from an ideal energy spectrum is suppressed can be obtained at the preceding stage of raw data decomposition.

In step S4, the system controller 43 controls the image generator 33 to perform image reconstruction processing (step S5). In step S5-1, the image generator 33 performs image reconstruction processing on the first reference substance raw data set, thereby generating a first reference substance image data set. The first reference substance image is an image representing the spatial distribution of the abundance ratio of the first reference substance to the second reference substance. Similarly, the image generator 33 performs image reconstruction processing on the second reference substance raw data set, thereby generating a second reference substance image data set. The second reference substance image is an image representing the spatial distribution of the abundance ratio of the second reference substance to the first reference substance. Image reconstruction processing may be performed by any reconstruction method as long as the image reconstruction method is applicable to a raw data set multiplied by the scaling coefficient. As this image reconstruction method, FBP (Filtered Back Projection), or CBP (Convolution Back Projection) is desirable.

The first and second reference substance image data sets are generated based on the low-tube-voltage raw data set multiplied by the correction coefficient regarding a low tube voltage, and the high-tube-voltage raw data set multiplied by the correction coefficient regarding a high tube voltage. Thus, in the first and second reference substance image data sets, noise arising from the energy difference of the actual energy spectrum of X-rays from an ideal energy spectrum is reduced, compared to a related art in which image reconstruction is executed based on a raw data set not multiplied by the correction coefficient according to the embodiment.

The display unit 37 displays the first reference substance image and second reference substance image. The display unit 37 may display a monochromatic X-ray image, density image, and effective atomic number image which have been generated by the image generator 33 based on the first reference substance image and second reference substance image.

An example of the operation of dual-energy CT scanning according to the embodiment has been explained.

In the above-described embodiment, the X-ray computed tomography imaging apparatus according to the embodiment includes a pair of X-ray tube 13 and X-ray detector 15. However, the embodiment is not limited to this. More specifically, the X-ray computed tomography imaging apparatus according to the embodiment may be equipped with two systems of X-ray tubes and X-ray detectors. In this case, in dual-energy CT scanning, the X-ray controller 25 controls the high-voltage generator to apply a low tube voltage to one X-ray tube, and also controls the high-voltage generator to apply a high tube voltage to the other X-ray tube. Accordingly, the data acquisition circuit 27 can acquire a low-tube-voltage raw data set and high-tube-voltage raw data set.

In the above description, the X-ray computed tomography imaging apparatus is of the so-called third generation. That is, the X-ray computed tomography imaging apparatus is of a rotate/rotate-type in which the X-ray tube 13 and X-ray detector 15 integrally rotate around the subject S. However, the X-ray computed tomography imaging apparatus according to the embodiment is not limited to this. For example, the X-ray computed tomography imaging apparatus may be of a stationary/rotate-type in which many X-ray detection elements arrayed in a ring are fixed and only the X-ray tube 13 rotates around the subject S.

As described above, the X-ray computed tomography imaging apparatus according to the embodiment includes the X-ray tube 13, high-voltage generator 23, X-ray detector 15, rotating frame 11, data acquisition circuit 27, and image generator 33. The X-ray tube 13 generates X-rays. The high-voltage generator 23 generates a tube voltage to be applied to the X-ray tube 13. The X-ray detector 15 detects X-rays which have been generated from the X-ray tube 13 and have passed through the subject S. The rotating frame 11 rotatably supports the X-ray tube 13 and X-ray detector 15. The data acquisition circuit 27 acquires raw data corresponding to the intensity of X-rays via the X-ray detector 15. Based on a plurality of raw data sets which have been acquired by the data acquisition circuit 27 and correspond to respective tube voltages, the image generator 33 generates a plurality of reference substance image data sets targeting respective reference substances contained in the subject S. More specifically, the image generator 33 generates a raw data set after scaling processing by applying, to a raw data set corresponding to each tube voltage, a correction coefficient for suppressing the discrepancy of the actual energy spectrum of X-rays detected by the X-ray detector 15 from an ideal X-ray energy spectrum. Based on a plurality of correction data sets corresponding to the respective tube voltages, the image generator 33 generates a plurality of reference substance image data sets.

With the above-described arrangement, the system controller 43 according to the embodiment executes raw data-based dual-energy processing. That is, the first reference substance raw data set and second reference substance raw data set are generated by performing raw data decomposition on two types of raw data sets (low-tube-voltage raw data and high-tube-voltage raw data) acquired by dual-energy CT scanning. The image generator 33 according to the embodiment can perform raw data decomposition after scaling processing in raw data-based dual-energy processing, as described above. Therefore, the embodiment can suppress deterioration of the accuracy of raw data decomposition arising from the discrepancy of an actual X-ray energy spectrum from an ideal X-ray energy spectrum in multi-energy CT scanning.

The embodiment can suppress deterioration of the image quality arising from the discrepancy of an actual X-ray energy spectrum from an ideal X-ray energy spectrum.

(First Modification)

In the above-described embodiment, a plurality of raw data sets corresponding to a plurality of tube voltage values are acquired by switching the tube voltage value. However, the embodiment is not limited to this. An X-ray computed tomography imaging apparatus according to the first modification acquires a plurality of raw data sets corresponding to a plurality of energy values by an X-ray detector having a multilayered structure. The X-ray computed tomography imaging apparatus according to the first modification will be described below. In the following description, the same reference numerals as those in the above-described embodiment denote building components having almost the same functions, and a repetitive description thereof will be made, only as needed.

An X-ray detector according to the first modification includes detectors of a plurality of layers. The energy of detected X-rays can be discriminated in accordance with the number of layers. For example, when a X-ray detector having a two-layered structure (a detector of a shallow layer and a detector of a deep layer) is used, X-rays of a low energy are detected by the detector of the shallow layer, and X-rays of a high energy are detected by the detector of the deep layer through the detector of the shallow layer.

The data acquisition circuit 27 acquires a plurality of raw data sets corresponding to respective energies based on electrical signals from the detectors of a plurality of layers. For example, the data acquisition circuit 27 acquires a raw data set corresponding to a low energy based on electrical signals from the detector of the shallow layer, and acquires a raw data set corresponding to a high energy based on electrical signals from the detector of the deep layer.

Based on a plurality of raw data sets corresponding to respective energies, the image generator 33 generates a plurality of reference substance image data sets targeting respective reference substances contained in the subject S. More specifically, the image generator 33 generates a correction data set for each of a plurality of energies by applying, to a raw data set corresponding to each tube voltage, a correction coefficient for suppressing the discrepancy of the actual energy spectrum of X-rays detected by the X-ray detector 15 from an ideal X-ray energy spectrum. Then, the image generator 33 generates a plurality of reference substance image data sets based on a plurality of correction data sets corresponding to the respective tube voltages. The correction coefficient calculation method and the reference substance image data set generation method are the same as those in the above-described embodiment, and a description thereof will not be repeated.

With this arrangement, the X-ray computed tomography imaging apparatus according to the first modification can execute multi-energy CT scanning by using the X-ray detector of a multilayered structure, and suppress deterioration of the accuracy of raw data decomposition arising from the discrepancy of an actual X-ray energy spectrum from an ideal X-ray energy spectrum.

The first modification can therefore suppress deterioration of the image quality arising from the discrepancy of an actual X-ray energy spectrum from an ideal X-ray energy spectrum.

(Second Modification)

In the above-described embodiment, the modality is the X-ray computed tomography imaging apparatus. However, the embodiment is not limited to this. A modality according to the second modification is a photon counting CT apparatus. The photon counting CT apparatus according to the second modification will be described below. In the following description, the same reference numerals as those in the above-described embodiment denote building components having almost the same functions, and a repetitive description thereof will be made, only as needed.

The X-ray detector 15 detects X-ray photons generated from the X-ray tube 13. The X-ray detector 15 includes a plurality of X-ray detection elements arrayed two-dimensionally. Typically, the X-ray detector 15 is implemented by a direct detection type compound semiconductor detector. Each X-ray detection element detects X-ray photons from the X-ray tube 13, and generates an electrical pulse (electrical signal) corresponding to the energy of the detected X-ray photons. More specifically, the X-ray detection element is constituted by a semiconductor diode obtained by attaching electrodes to the two ends of a semiconductor. X-ray photons entering the semiconductor are converted into electron-hole pairs. The number of electron-hole pairs generated by the incidence of one X-ray photon depends on the energy of the incident X-ray photon. An electron and hole are attracted to a pair of electrodes formed at the two ends of the semiconductor. The pair of electrodes generates an electrical pulse having a peak value corresponding to the charges of an electron-hole pair. One electrical pulse has a peak value corresponding to the energy of an incident X-ray photon. As the semiconductor material according to the embodiment, a substance of a relatively large atomic number capable of efficiently converting X-ray photons into hole-electron pairs is preferably used. Known examples of a semiconductor material suitable for photon counting CT are CdTe and CdZnTe. Note that the X-ray detector 15 according to the embodiment is not limited to a direct detection type compound semiconductor detector, and may be an indirect detection type detector. As the indirect detection type X-ray detector 15, a type obtained by combining a scintillator and photosensor is applicable.

In accordance with a control signal from the gantry controller 21, the data acquisition circuit 27 acquires, for a plurality of energy bands, digital data (to be referred to as count data hereinafter) representing the count of the number of X-ray photons detected by the X-ray detector 15.

The pre-processor 31 performs pre-processing such as logarithmic transformation on the count data from the gantry 10. Raw data after pre-processing is also called projection data. The pre-processing includes various correction processes such as logarithmic transformation, X-ray intensity correction, and offset correction.

Based on a plurality of count data sets corresponding to respective energy bands, the image generator 33 generates a plurality of reference substance image data sets targeting respective reference substances contained in the subject. More specifically, the image generator 33 generates a correction data set for each of a plurality of energy bands by applying, to a count data set corresponding to each energy band, a correction coefficient for suppressing the discrepancy of the actual energy spectrum of X-rays detected by the X-ray detector 15 from an ideal X-ray energy spectrum. Then, the image generator 33 generates a plurality of reference substance image data sets based on a plurality of correction data sets corresponding to the respective energy bands.

An example of the operation of photon counting CT scanning to be performed under the control of the system controller 43 according to the second modification will be explained below. FIG. 3 is a flowchart showing an example of the typical operation of photon counting CT scanning to be performed under the control of the system controller 43.

As shown in FIG. 3, the system controller 43 controls the gantry controller 21 to execute photon counting CT scanning (step S11). In step S11, the gantry controller 21 starts photon counting CT scanning in response to a start instruction from the user via the input unit 39 or the like. In photon counting CT scanning, the gantry controller 21 controls the rotation driving unit 19 to rotate the rotating frame 11 at a predetermined angular velocity. Also, the gantry controller 21 controls the X-ray controller 25 to control the high-voltage generator 23 so as to apply a predetermined high voltage to the X-ray tube 13. The gantry controller 21 controls the data acquisition circuit 27 to acquire count data regarding each of a plurality of energy bands for each view. The number of energy bands suffices to be arbitrarily two or more, and is assumed to be two for descriptive convenience. Here, count data regarding an energy band on the low energy side will be called low-energy count data Low(ch,seg,view), and count data regarding an energy band on the high energy side will be called high-energy count data High(ch,seg,view). The low-energy count data set Low(ch,seg,view) and high-energy count data set High(ch,seg,view) are represented as functions each of a channel "ch", segment "seg", and view "view".

After performing step S11, the system controller 43 controls the pre-processor 31 to perform pre-processing (step S12). In step S12-1, the pre-processor 31 performs pre-processing on the low-energy count data set from the data acquisition circuit 27, and outputs a low-energy count data set inLow(ch,seg,view) after pre-processing. Similarly, in step S12-2, the pre-processor 31 performs pre-processing on the high-energy count data set from the data acquisition circuit 27, and outputs a high-energy count data set inHigh (ch,seg,view) after pre-processing.

After performing step S12, the system controller 43 controls the image generator 33 to perform scaling processing (step S13). In step S13-1, the image generator 33 multiplies, by a correction coefficient, the low-energy count data set inLow(ch,seg,view) after pre-processing, and outputs a low-energy count data set outLow(ch,seg,view) after scaling processing. Similarly, in step S13-2, the image generator 33 multiplies, by a correction coefficient, the high-energy count data set inHigh(ch,seg,view) after pre-processing, and outputs a high-energy count data set outHigh(ch,seg,view) after scaling processing.

The image generator 33 determines the correction coefficient for each energy band. The correction coefficient is a coefficient for suppressing a noise component arising from the energy difference of the actual energy spectrum of X-rays from an ideal energy spectrum for each energy band. The correction coefficient regarding photon counting CT scanning can be calculated similarly to a correction coefficient regarding multi-energy CT scanning, so details of the correction coefficient regarding photon counting CT scanning will be omitted.

After performing step S13, the system controller 43 controls the image generator 33 to perform raw data decomposition (step S14). In step S14, the image generator 33 performs raw data decomposition on the low-energy count data outLow(ch,seg,view) after scaling processing and the high-energy count data outHigh(ch,seg,view) after scaling processing, thereby generating a first data set (to be referred to as a first reference substance raw data set hereinafter) corresponding to the first reference substance, and a second data set (to be referred to as a second reference substance raw data set hereinafter) corresponding to the second reference substance.

As described above, raw data decomposition targets the low-energy count data set and high-energy count data set multiplied by the correction coefficients for suppressing a noise component arising from the energy difference of the actual energy spectrum of X-rays from an ideal energy spectrum. That is, a raw data set in which the discrepancy of the actual energy spectrum of X-rays from an ideal energy spectrum is suppressed can be obtained at the preceding stage of raw data decomposition.

In step S14, the system controller 43 controls the image generator 33 to perform image reconstruction processing (step S15). In step S15-1, the image generator 33 performs image reconstruction processing on the first reference substance raw data set, thereby generating a first reference substance image data set. Similarly, the image generator 33 performs image reconstruction processing on the second reference substance raw data set, thereby generating a second reference substance image data set.

An example of the operation of photon counting CT scanning according to the second modification has been explained.

With this arrangement, the photon counting CT apparatus according to the second modification regards photon counting CT scanning as multi-energy CT scanning, and can suppress deterioration of the accuracy of raw data decomposition arising from the discrepancy of an actual X-ray energy spectrum from an ideal X-ray energy spectrum.

Hence, the second modification can suppress deterioration of the image quality arising from the discrepancy of an actual X-ray energy spectrum from an ideal X-ray energy spectrum.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography imaging apparatus comprising:
   an X-ray tube configured to generate X-rays;
   a high-voltage generator configured to generate a tube voltage to be applied to the X-ray tube;
   an X-ray detector configured to detect X-rays which have been generated from the X-ray tube and have passed through a subject;
   a support mechanism configured to rotatably support the X-ray tube;
   a data acquisition unit configured to acquire detection data corresponding to an intensity of the detected X-rays via the X-ray detector; and
   an image generator configured to generate, based on a plurality of detection data sets which have been acquired by the data acquisition unit and correspond to respective tube voltages, a plurality of reference substance image data sets targeting respective reference substances contained in the subject,
   wherein the image generator generates a correction data set for each of the plurality of tube voltages by applying, to a detection data set corresponding to each of the tube voltages, a correction coefficient for suppressing a discrepancy of an actual energy spectrum of the X-rays detected by the X-ray detector from a predetermined X-ray energy spectrum, and generates the plurality of reference substance image data sets based on a plurality of correction data sets corresponding to the respective tube voltages.

2. The apparatus according to claim 1, wherein
   the plurality of tube voltages include a first tube voltage, and a second tube voltage higher than the first tube voltage,
   the plurality of reference substance image data sets include a first reference substance image data set targeting a first reference substance, and a second reference substance image data set targeting a second reference substance, and
   the image generator generates a first correction data set by applying, to the first detection data set, a first correction coefficient regarding the first tube voltage, generates a second correction data set by applying, to the second detection data set, a second correction coefficient regarding the second tube voltage, and generates the first reference substance image data set and the second reference substance image data set based on the first correction data set and the second correction data set.

3. The apparatus according to claim 2, wherein the image generator generates a first data set corresponding to the first reference substance and a second data set corresponding to the second reference substance by performing data decomposition on the first correction data set and the second correction data set, generates the first reference substance image data set by performing image reconstruction processing on the first data set, and generates the second reference substance image data set by performing image reconstruction processing on the second data set.

4. The apparatus according to claim 3, wherein the image reconstruction processing includes filtered back projection.

5. The apparatus according to claim 2, wherein
   the first correction coefficient is defined by a ratio of a scaling coefficient targeting an ideal energy spectrum of X-rays regarding the first tube voltage to a scaling coefficient targeting an energy spectrum of X-rays actually detected by the X-ray detector, and
   the second correction coefficient is defined by a ratio of a scaling coefficient targeting an ideal energy spectrum of X-rays regarding the second tube voltage to a scaling coefficient targeting an energy spectrum of X-rays actually detected by the X-ray detector.

6. The apparatus according to claim 1, further comprising a display unit configured to display the plurality of reference substance images.

7. A photon counting CT apparatus comprising:
   an X-ray tube configured to generate X-rays;
   a high-voltage generator configured to generate a tube voltage to be applied to the X-ray tube;
   an X-ray detector configured to detect X-ray photons which have been generated from the X-ray tube and have passed through a subject;
   a support mechanism configured to rotatably support the X-ray tube;
   a data acquisition unit configured to acquire, for each of a plurality of energy bands, count data corresponding to a count of the detected X-ray photons via the X-ray detector; and
   an image generator configured to generate, based on a plurality of count data sets which have been acquired by the data acquisition unit and correspond to the respective energy bands, a plurality of reference substance image data sets targeting respective reference substances contained in the subject,
   wherein the image generator generates a correction data set for each of the plurality of energy bands by applying, to a count data set corresponding to each of the energy bands, a correction coefficient for suppressing a discrepancy of an actual energy spectrum of the X-rays detected by the X-ray detector from a predetermined X-ray energy spectrum, and generates the plurality of reference substance image data sets based on a plurality of correction data sets corresponding to the respective energy bands.

8. The apparatus according to claim 7, wherein
   the plurality of energy bands include a first energy band, and a second energy band higher than the first energy band,
   the plurality of reference substance image data sets include a first reference substance image data set targeting a first reference substance, and a second reference substance image data set targeting a second reference substance, and the image generator generates a first correction data set by applying, to the first count data set, a first correction coefficient regarding the first energy band, generates a second correction data set by applying, to the second count data set, a second correction coefficient regarding the second energy band, and generates the first reference substance image data set and the second reference substance image data set based on the first correction data set and the second correction data set.

9. The apparatus according to claim 8, wherein the image generator generates a first data set corresponding to the first reference substance and a second data set corresponding to the second reference substance by performing data decomposition on the first correction data set and the second correction data set, generates the first reference substance image data set by performing image reconstruction processing on the first data set, and generates the second reference substance image data set by performing image reconstruction processing on the second data set.

10. The apparatus according to claim 9, wherein the image reconstruction processing includes filtered back projection.

11. The apparatus according to claim 8, wherein
the first correction coefficient is defined by a ratio of a scaling coefficient targeting an ideal energy spectrum of X-rays regarding the first energy band to a scaling coefficient targeting an energy spectrum of X-rays actually detected by the X-ray detector, and the second correction coefficient is defined by a ratio of a scaling coefficient targeting an ideal energy spectrum of X-rays regarding the second energy band to a scaling coefficient targeting an energy spectrum of X-rays actually detected by the X-ray detector.

12. The apparatus according to claim 7, further comprising a display unit configured to display the plurality of reference substance images.

* * * * *